United States Patent [19]

Ise et al.

[11] Patent Number: 5,399,551
[45] Date of Patent: Mar. 21, 1995

[54] ENHANCER FOR THE ANTIANEMIA EFFECT OF ERYTHROPOIETIN AND METHOD OF AUGMENTING THE ANTIANEMIA EFFECT OF ERYTHROPOIETIN

[75] Inventors: Michihito Ise, Kawagoe; Hideo Hayashi, Tokyo, both of Japan

[73] Assignee: Kureha Chemical Industry Co., Ltd., Japan

[21] Appl. No.: 137,789

[22] Filed: Oct. 19, 1993

[30] Foreign Application Priority Data

Oct. 29, 1992 [JP] Japan .................. 4-314181

[51] Int. Cl.⁶ .................. A61K 37/10; B01J 20/02
[52] U.S. Cl. .................. 514/8; 502/416; 502/417; 514/814; 424/125
[58] Field of Search .................. 514/8, 814, 12; 502/416, 417, 418, 426, 427; 424/125

[56] References Cited

U.S. PATENT DOCUMENTS 4,681,764  7/1987  Endo .................. 424/125

FOREIGN PATENT DOCUMENTS 0029715  6/1981  European Pat. Off. .
0178665  4/1986  European Pat. Off. .
5049694  3/1993  Japan .

OTHER PUBLICATIONS

Database WPI, Week 8302, Derwent Publications Ltd., AN 83–020708k abstract.

*Primary Examiner*—Michael G. Wityshyn
*Assistant Examiner*—Ralph Gitomer
*Attorney, Agent, or Firm*—Parkhurst, Wendel & Rossi

[57] ABSTRACT

There is disclosed an enhancer for the antianemia effect of erythropoietin using a spherical carbon as an active ingredient in an amount effective for treating anemia in combination with erythropoietin. The enhancer is orally administered. The antianemia effect of erythropoietin can be remarkably enhanced, the dosage of erythropoietin can be remarkably decreased, and side effects from erythropoietin can be remarkably reduced. There is further disclosed a method of augmenting the antianemia effect of erythropoietin by administering to a patient an effective amount of a spherical carbon in combination with a portion of an effective amount of erythropoietin for treating anemia.

12 Claims, No Drawings

ENHANCER FOR THE ANTIANEMIA EFFECT OF ERYTHROPOIETIN AND METHOD OF AUGMENTING THE ANTIANEMIA EFFECT OF ERYTHROPOIETIN

BACKGROUND OF THE INVENTION (1) Field of the Invention

The present invention relates to an enhancer comprising a spherical carbon as an active ingredient for augmenting the antianemia effect of erythropoietin, especially recombinant erythropoietin (recombinant human EPO: hereinafter sometimes referred to as "rHuEPO").

(2) Description of the Related Art

Through the development of gene engineering, rHuEPO preparations came to be used for treating anemia. Erythropoietin is one of the erythropoiesis-stimulating factors existing in a living body; the shortage of erythropoietin is one cause of anemia. The rHuEPO has been chemically, immunologically, and biologically confirmed to be identical to human erythropoietin.

The rHuEPO is a glycoprotein with a molecular weight of approximately 30,000 containing 165 amino acid residues which have two internal disulfide bonds linking the positions 7 and 161 and positions 29 and 33 and wherein three N-glucoside type saccharide chains are bound to the 24th, 38th, and 83rd asparagines and one O-glucoside type saccharide chain is bound to the 126th serine. There are some rHuEPOs dependent on the structures of saccharide chains. Examples of rHuEPOs that are now available commercially are Epogen TM and Espo TM. (See Seigo IWAKAWA, IGAKUNO AYUMI, Vol. 155, No. 10, pp. 631–633, 1990.)

Usually, when anemia becomes severe, the concentration of erythropoietin in blood becomes high. In renal anemia patients, however, in comparison with anemia patients having a normal renal function, there are not only many cases wherein the concentration of erythropoietin in blood is low, but also there are many cases wherein the erythropoiesis-inhibiting factor is present. Thus, a large amount of rHuEPO is needed in order to increase hematocrit as expected.

The rHuEPO causes, however, side effects such as hypertension, headaches, hypertensive encephalopathy, cerebral infarctions or myocardial infarctions due to thrombosis, closure of the retinal venous, obstruction of shunts, or lowering of dialysis efficiency. In addition, allergic or anaphylaxis-like symptoms of rHuEPO, such as lowering of blood pressure, arthralgia, itching, edema, red eyes, oppressive feeling in the chest, bleeding fleck, etc., are observed. Further, transitory and slight pyrexia, rashes, or hepatic disorders may sometimes be observed. Hypertension due to side effects is believed to be caused by the increase in peripheral blood vessel resistance due to the constriction of the peripheral blood vessel and the rise in blood viscosity.

SUMMARY OF THE INVENTION

It is an object of the present invention to provide an enhancer for the antianemia effect of erythropoietin, the enhancer comprising a spherical carbon as an active ingredient.

It is another object of the present invention to provide a method of augmenting the antianemia effect of erythropoietin wherein the side effects of erythropoietin are eliminated.

The present inventors energetically investigated a method of inhibiting the side effects discussed above caused by the administration of rHuEPO. As a result, the present inventors have discovered that the combined administration of a spherical carbon with rHuEPO unexpectedly decreases the required dosage of rHuEPO and permits avoidance or reduction of the side effects discussed above while maintaining the antianemia effect of rHuEPO. The present invention is based on this finding.

In order to achieve these objects, the present invention provides an enhancer for the antianemia effect of erythropoietin comprising a spherical carbon as an active ingredient.

The present invention further provides a method of augmenting the antianemia effect of erythropoietin comprising administering to a patient an effective amount of a spherical carbon in combination with a portion of an effective amount of erythropoietin for the treatment of anemia.

DETAILED DESCRIPTION OF PREFERRED EMBODIMENTS

The spherical carbon used as an active ingredient in the present invention is not particularly limited as long as the spherical carbon is an activated carbon having a spherical shape that can be used for medical treatment. Although a medical activated carbon powder is generally useful as an antidote, it is liable to cause constipation as a side effect. This is a critical problem because constipation at the time of illness is dangerous.

The spherical carbon used in the present invention has a particle diameter ranging from 0.05 to 2 mm. When the diameter is less than 0.05 mm, side effects such as constipation or the like are not sufficiently eliminated. On the other hand, when the diameter is over 2 mm, oral administration of the spherical carbon becomes difficult, and the desired pharmacological effect does not appear quickly.

The shape of the spherical carbon is an important factor for obtaining satisfactory medical effects of the present invention, and thus it is necessary that the spherical carbon has a substantially spherical shape.

Any raw materials for activated carbon may be used for producing the spherical carbon of the present invention. Although examples of such raw materials that can be used to produce the spherical carbon include sawdust, coal, coconut-shells, petroleum pitches, coal pitches, and synthetic organic high polymers, petroleum hydrocarbons are preferred. In the present invention, it is preferred to use an activated spherical carbon and/or a spherical carbonaceous adsorbent as the spherical carbon.

Particles of an activated spherical carbon that can be used in the present invention have a diameter of 0.05 to 2 mm.

A fundamental method of producing the activated spherical carbon according to the present invention comprises forming a raw material into fine spherical particles, carbonizing the spherical particles, and then activating the carbonized particles.

Various activation methods can be carried out, for example, using steam, chemicals, air, or carbon dioxide.

The activated spherical carbon particles can be produced, for example, by either of three methods. A first method comprises forming a raw material powder into fine spherical particles using a binder such as pitch, carbonizing the particles by baking the particles in an inert atmosphere at 600° to 1000° C., and then activating the carbonized particles in an atmosphere of steam at 850° to 1000° C. A second method comprises forming melted pitch into fine spherical particles, oxidizing the particles in an atmosphere containing oxygen to render the particles infusible, and then carbonizing and activating the infusible particles under the same conditions as those in the above first method, as disclosed in, for example, Japanese Patent Publication No. 51-76 (see U.S. Pat. No. 3,917,806). A third method comprises melt-extruding pitch to form a string-like pitch, breaking the string-like pitch, casting the broken product into hot water to obtain spherical particles, oxidizing the particles in an atmosphere containing oxygen to render the particles infusible, and then carbonizing and activating the infusible particles under the same conditions as those in the above first method, as disclosed in, for example, Japanese Patent Publication No. 59-10930 (see U.S. Pat. No. 4,420,443).

The spherical carbonaceous adsorbent that can be used in the present invention preferably comprises activated carbon particles having a diameter of 0.05 to 2 mm, a pore radius of not more than 80 angstroms in a pore amount of 0.2 to 1.0 ml/g, a total amount of acidic groups (A) of 0.30 to 1.20 meq/g, a total amount of basic groups (B) of 0.20 to 0.70 meq/g, and a ratio of the total amount of acidic groups (A)/total amount of basic groups (B) of 0.40 to 2.5. An example of such spherical carbonaceous adsorbents is disclosed in Japanese Patent Publication No. 62-11611 (see the specification of U.S. Pat. No. 4,681,764).

The spherical carbonaceous adsorbent can be produced by oxidizing and reducing, at a high temperature, activated spherical carbon particles having a diameter of 0.05 to 2 mm and a pore radius of not more than 80 angstroms in a pore amount of 0.2 to 1.0 ml/g. Oxidation and reduction at a high temperature are preferably carried out so that the total amount of acidic groups (A) and the total amount of basic groups (B) of the spherical carbonaceous adsorbent obtained are adjusted within the ranges of 0.30 to 1.20 meq/g and 0.20 to 0.70 meq/g, respectively, and the ratio of (A)/(B) is adjusted within the range of 0.40 to 2.5.

The total amount of acidic groups (A) and the total amount of basic groups (B) are determined by the following usual methods.

(a) Total amount of acidic groups (A)

One gram of pulverized adsorbent specimen which passed through a Taylor standard sieve of 200 mesh is added to 50 ml of a 0.05 N aqueous NaOH solution, followed by shaking for 48 hours. The resultant mixture is filtered to remove the adsorbent, and the filtrate is neutralized by titration. The total amount of acidic groups (A) is determined by the amount of NaOH consumed by the titration and is expressed in units of meq/g of specimen.

(b) Total amount of basic groups (B)

One gram of pulverized adsorbent specimen which passed through a Taylor standard sieve of 200 mesh is added to 50 ml of a 0.05 N aqueous HCl solution, followed by shaking for 24 hours. The resultant mixture is filtered to remove the specimen, and the filtrate is neutralized by titration. The total amount of basic groups (B) is determined by the amount of HCl consumed by the titration and is expressed in units of meq/g of specimen.

High temperature oxidation is performed by heating the particles at a high temperature in an atmosphere containing oxygen, which is formed by using pure oxygen, nitrogen oxides, or air as an oxygen source.

High temperature reduction is performed by heating the particles at a high temperature in an atmosphere of a gas that is inert to carbon. The atmosphere of a gas that is inert to carbon is formed by using nitrogen, argon, helium, or a mixture thereof.

Oxidation heating is preferably carried out at 300° to 700° C., more preferably at 400° to 600° C., in an atmosphere containing preferably 0.5 to 25% by volume of oxygen, more preferably 3 to 10% by volume of oxygen. Reduction is preferably carried out at 700° to 1100° C., more preferably at 800° to 1000° C., in an atmosphere of nitrogen.

The enhancer of the present invention is used in combination with any erythropoietin having an antianemia effect, especially rHuEPO. As the rHuEPO, rHuEPOs can be used that, for example, are produced using gene engineering from mammalian host cells which are transformed with vectors containing the gene encoding at least the active site of human erythropoietin.

When the combined effect of the oral administration of the spherical carbonaceous adsorbent with the subcutaneous administration of rHuEPO to anemic rats was examined in comparison with the subcutaneous administration of an effective amount of the rHuEPO alone, a surprising phenomenon was found. In the case of combining rHuEPO with the spherical carbon, even if the dosage of rHuEPO was reduced to half of the effective amount, the same effect was shown as for the case of the subcutaneous administration of the effective amount of the rHuEPO alone. That is, the spherical carbon was found to enhance the antianemia effect of rHuEPO and to be useful as an enhancer for the antianemia effect of rHuEPO. In addition, and most importantly, no abnormality was induced when the enhancer of the present invention was administered to normal rats.

The enhancer of the antianemia effect of erythropoietin according to the present invention can be administered orally. The dosage depends on the subject (animal or human), the age, the differences among subjects, the conditions of the disease, etc. For example, the oral dosage of the spherical carbon for humans is within the range of 0.2 to 20 g per day. The dosage may be administered at one time or in 2 to 4 portions. The dosage may be adjusted appropriately according to the symptoms.

Thus, the spherical carbon can be administered as it is or in the form of a pharmaceutical composition as an enhancer for the antianemia effect of erythropoietin.

The spherical carbon may be administered as a medicine to patients in any desired form such as granules, tablets, sugar-coated tablets, capsules, stick packages, divided packages, suspensions, or the like.

When the particles are administered in the form of capsules, ordinary gelatin capsules or, if necessary, enteric capsules may be used. When the carbon particles are used in the form of granules, tablets, or sugar-coated tablets, the form must be disintegrated into the original fine spherical particles in the alimentary canal of a patient.

Although the content of the spherical carbon in a pharmaceutical composition may be varied according to symptoms and other factors, it is usually present in an amount of 1 to 99% by weight, and preferably, 10 to 99% by weight of the composition.

Erythropoietin may be administered by the usual method and, generally in the form of injection; erythropoietin is administered intravenously, subcutaneously, or intraperitoneally. An example of the usual administration methods when rHuEPO alone is administered follows.

The rHuEPO is administered intravenously as slowly as possible in 3000 units at a time, three times a week, for an adult person. Upon the recognition of a recovery effect from anemia, erythropoietin is administered, as a maintenance dose, in 1500 units at a time, 2 to 3 times a week, or in 3000 units at a time, twice a week. The target hematocrit of recovery from anemia is about 30%. In order to prevent side effects, care must be taken so that the hematocrit increases less than 1% in a week.

When the enhancer of the present invention is used in combination with the erythropoietin, the dosage of erythropoietin (rHuEPO) may be 5 to 90% and preferably 30 to 90%, of the above dosage where rHuEPO alone is used as the antianemia agent.

The administration period of the spherical carbon enhancer of the present invention and the administration period of erythropoietin that is the antianemia agent can be arranged optionally. For example, the administration periods may be sequential or concurrent. They may be concurrent in only a part of the period. Further, such administration schedules can be optionally combined or repeated.

When an rHuEPO antianemia agent is used in combination with the spherical carbon enhancer of the present invention, the antianemia effect of rHuEPO can be remarkably enhanced and the dosage of erythropoietin can be remarkably decreased. Therefore, side effects from rHuEPO are remarkably reduced.

Although the present invention will be more precisely explained below with reference to examples, the invention is not limited to these examples.

PRODUCTION EXAMPLE 1

Preparation of a Spherical Carbonaceous Adsorbent

An autoclave equipped with a stirrer was charged with 100 g of naphthalene and 300 g of pitch (H/C=0.55, flow point 220° C.) having an anisotropic region that was not localized under a polarization microscope. The resultant mixture was mixed well at 180° C. to form a solution. Into the resulting solution, 1200 g of 0.5% polyvinyl alcohol aqueous solution was added. Then, the mixture was vigorously stirred at 140° C. for 30 minutes and cooled to room temperature under stirring to form a dispersion of spherical particles. After a large part of water was separated from the dispersion, the remaining spherical particles were treated with hexane in an extractor to remove naphthalene contained therein by extraction and then dried by an air flow. The thus-obtained particles were heated to 300° C. at a rate of 25° C./h by a flow of heated air in a fluidized bed system, and were further maintained for 2 hours at 300° C. to obtain infusible oxygen-containing spherical particles. The particles were then heated to 900° C. in steam and kept at 900° C. for 2 hours in steam so as to carbonize and activate the particles to obtain porous activated spherical carbon. The activated spherical carbon had a diameter of 0.05 to 1.0 mm and a pore radius of not more than 80 angstroms in a pore amount of 0.755 ml/g, which was determined by a methanol adsorption method using an automatic adsorption measuring apparatus.

The thus-obtained activated spherical carbon particles were heated to 600° C. in an atmosphere containing 3% by volume of oxygen, and were further heated at 600° C. for 3 hours in the same atmosphere using a fluidized bed. Then, the particles were further heated to 950° C. in a nitrogen atmosphere and kept at 950° C. for 30 minutes in the same atmosphere to obtain an intended spherical carbonaceous adsorbent (hereinafter referred to as "Sample 1").

The spherical carbonaceous adsorbent particles had a diameter of 0.05 to 1 mm, a pore radius of not more than 80 angstroms in a pore amount of 0.751 ml/g (which was determined by the methanol adsorption method using an automatic adsorption measuring apparatus), a total amount of acidic groups (A) of 0.542 meq/g, a total amount of basic groups (B) of 0.525 meq/g, and a ratio of the total amount of acid groups (A)/total amount of basic groups (B) of 1.03.

In acute toxicity tests of the spherical carbonaceous adsorbent administered orally to male and female rats (Cpb: WU: Wistar Random), no abnormality was observed even at the maximum dosage (5000 mg/kg for male and female rats) based on the Guidelines for Toxicity Studies of Drugs (Notification No. 118 of the Pharmaceutical Affairs Bureau, Ministry of Health and Welfare, Japanese Government, Feb. 15, 1984).

EXAMPLE 1

Enhancing Effect for the Antianemia Effect in Anemic Rats

Sample 1 obtained in Production Example 1 was used as a spherical carbonaceous adsorbent to enhance the antianemia effect of erythropoietin.

As the rHuEPO, epoetin alfa (genetic recombination) [Espo TM of Kirin Brewery KK] was used. Epoetin alfa is a glycoprotein (molecular weight about 30,000) containing 165 amino acid residues ($C_{809}H_{1301}N_{229}O_{240}S_5$; molecular weight; 18,135.96) which is produced from Chinese hamster ovary cells through the expression of erythropoietin genome DNA originating from human liver cells.

Male Wistar rats (body weight about 260 g) were used and renal anemia was induced by partial nephrectomy. On the 9th day after the operation, hematocrit was measured and the rats were divided into six groups, a control group (C group), a spherical carbonaceous adsorbent-administering group (A group), an rHuEPO alone-administering group (E group), a half amount of rHuEPO-administering group (E½ group), a combination administration group of a spherical carbonaceous adsorbent and a half amount of rHuEPO (AE½ group), and a combination administration group of a spherical carbonaceous adsorbent and a ¼ quantity of rHuEPO (AE¼ group), so that there was no deviation in the hematocrit among the groups.

The test period was three weeks. A feed for rats was freely given to each group. Drug administration to each group was carried out as follows.

C group: Physiological saline [0.4 ml/kg (rat body weight)] was administered subcutaneously twice a week.

A group: A feed containing 5% spherical carbonaceous adsorbent was freely given.

E group: A solution of rHuEPO in physiological saline [60 unit/kg (rat: body weight)] was administered subcutaneously twice a week.

E½ group: A solution of rHuEPO in physiological saline [30 unit/kg (rat body weight)] was administered subcutaneously twice a week.

AE½ group: While a feed containing 5% spherical carbonaceous adsorbent was freely given, a solution of rHuEPO in physiological saline [30 unit/kg (rat body weight)] was administered subcutaneously twice a week.

AE⅓ group: While a feed containing 5% spherical carbonaceous adsorbent was freely given, a solution of rHuEPO in physiological saline [20 unit/kg (rat body weight)] was administered subcutaneously twice a week.

After three weeks following the start of the test period, blood was collected from the jugular vein of each rat and the hematocrit was measured. The results appear in Table 1.

TABLE 1

| | | At the Start Hematocrit (%) | At the end of the Test period Hematocrit (%) | Signif. dif. from C gr. | Signif. dif. from E gr. | Signif. dif. from E1/2 gr. | Signif. dif. from A gr. |
|---|---|---|---|---|---|---|---|
| C | group | 43 ± 1 | 36 ± 3 | | | | |
| A | group | 44 ± 2 | 38 ± 2 | N.S. | | | |
| E | group | 43 ± 2 | 46 ± 2 | $P < 0.01$ | | $P < 0.05$ | $P < 0.01$ |
| E1/2 | group | 44 ± 1 | 41 ± 3 | $P < 0.05$ | | | |
| AE1/2 | group | 44 ± 2 | 46 ± 3 | $P < 0.01$ | N.S. | $P < 0.05$ | $P < 0.01$ |
| AE1/3 | group | 45 ± 1 | 44 ± 4 | | N.S. | | |

Value: mean ± S.D. (five rats for each group except for the AE1/3 group; three rats for the AE1/3 group)
Significant difference test: P value in t-test (N.S. means "no significant difference.")
Signif. dif. from C gr. etc. = Significant difference from C group etc.

In the C group, there was a lowering of hematocrit in comparison with hemocrit at the start of the test; the progression of anemia was observed. On the other hand, in the A group, hemocrit lowering was slightly inhibited. In the E group, the hematocrit increased in comparison with the hemocrit at the start of the test while the anemia was inhibited. In contrast, in the E½ group, the hematocrit decreased slightly in comparison with that at the start of the test. In the AE½ group (representative of the present invention), however, the hematocrit increased in comparison with that at the start of the test, the level was higher than that of the E½ group, and the anemia was inhibited at the same degree as in the E group. There was no significant difference between the E group and the AE½ group. There was also no significant difference between the E group and the AE⅓ group. That is, by using in combination the spherical carbonaceous adsorbent, even with a half or a third of the administration amount of the rHuEPO, it was shown that the same effect was exhibited as when administering only rHuEPO. The hematocrit of normal rats is from 43 to 49%. The dosage of the enhancer for the antianemia effect (the spherical carbonaceous adsorbent) was about 18.8 g/kg(rat body weight)/week (calculated on the basis of the feed consumed by the rats).

FORMULATION EXAMPLE 1

Capsule

Two hundred milligrams of the spherical carbonaceous adsorbent obtained in Production Example 1 were enclosed in a gelatin capsule to provide a capsule.

FORMULATION EXAMPLE 2

Stick Package

Two grams of the spherical carbonaceous adsorbent obtained in Production Example 1 were put into a stick made of a laminated film (constitution: glassine paper/polyethylene/aluminum foil/polyethylene/polyvinylidene chloride, thickness: 74 ±8 μm) and heat-sealed to produce a stick package.

What is claimed is:

1. A method of augmenting the antianemia effect of erythropoietin being administered to a patient afflicted with anemia, said method comprising administering to said patient an erythropoietin antianemia-effect augmenting amount of a spherical carbon in combination with a portion of an effective amount of erythropoietin normally required to treat anemia in said patient in the absence of said spherical carbon, thereby decreasing the dosage of erythropoietin normally required to treat anemia in said patient to said portion of an effective amount and reducing the side effects caused by erythropoietin, said spherical carbon being a spherical carbonaceous adsorbent having a particle diameter of about 0.05 to about 2 mm, a pore radius of not more than 80 angstroms in a pore amount of about 0.2 to about 1.0 ml/g, a total amount of acidic groups of about 0.30 to about 1.20 meq/g, a total amount of basic groups of about 0.20 to about 0.70 meq/g, and a ratio of the total amount of acidic groups to the total amount of basic groups (B) of about 0.40:1 to about 2.5:1.

2. The method of claim 1, wherein the amount of erythropoietin administered is 5 to 90% of the amount of erythropoietin normally administered in the absence of said spherical carbon.

3. The method of claim 1, wherein said spherical carbon is administered orally.

4. The method of claim 1, wherein said spherical carbon is administered in a quantity of 0.2 to 20 g per day.

5. A method of augmenting the antianemia effect of erythropoietin comprising administering to a patient afflicted with anemia an effective amount of a spherical carbon in combination with a portion of an effective amount of erythropoietin normally required for the treatment of anemia in said patient in the absence of said spherical carbon, thereby decreasing the dosage of erythropoietin normally required to treat anemia in said patient to said portion of an effective amount and reducing the side effects caused by erythropoietin, said spherical carbon being a spherical carbonaceous adsorbent having a particle diameter of about 0.05 to about 2 mm, a pore radius of not more than 80 angstroms in a pore amount of about 0.2 to about 1.0 ml/g, a total amount of acidic groups of about 0.30 to about 1.20 meq/g, a total amount of basic groups of about 0.20 to about 0.70 meq/g and a ratio of the total amount of acidic groups to the total amount of basic groups of about 0.40:1 to about 2.5:1.

6. The method of claim 5, wherein said portion is 5 to 90% of the amount of erythropoietin normally administered in the absence of said spherical carbon.

7. The method of claim 5, wherein said spherical carbon is administered orally.

8. The method of claim 5, wherein said spherical carbon is administered in a quantity of 0.2 to 20 g per day.

9. A method of combination therapy for treating a patient suffering from anemia which comprises administering to said patient an effective amount of spherical carbon in combination with a portion of an effective amount of erythropoietin normally required to treat anemia in said patient in the absence of said spherical carbon, thereby decreasing the dosage of erythropoietin normally required to treat anemia in said patient to said portion of an effective amount and reducing the side effects caused by erythropoietin, said spherical carbon being a spherical carbonaceous adsorbent having a particle diameter of about 0.05 to about 2 mm, a pore radius of not more than 80 angstroms in a pore amount of about 0.2 to about 1.0 ml/g, a total amount of acidic groups of about 0.30 to about 1.20 meq/g, a total amount of basic groups of about 0.20 to about 0.70 meq/g, and a ratio of the total amount of acidic groups to the total amount of basic groups of about 0.40:1 to about 2.5:1.

10. The method of claims 9, wherein said portion is 5 to 90% of the amount of erythropoietin normally administered in the absence of said spherical carbon.

11. The method of claim 9, wherein said spherical carbon is administered orally.

12. The method of claim 9, wherein said spherical carbon is administered in a quantity of 0.2 to 20 g per day.

* * * * *

UNITED STATES PATENT AND TRADEMARK OFFICE
CERTIFICATE OF CORRECTION

PATENT NO. : 5,399,551
DATED : March 21, 1995
INVENTOR(S) : Michihito ISE

It is certified that error appears in the above-indentified patent and that said Letters Patent is hereby corrected as shown below:

column 1, line 36, "IGAKUNO AYUMI" should be amended to --IGAKU NO AYUMI--.

column 8, claim 1, line 39, "(B)" should be deleted.

column 8, claim 1, line 66, "meq/g and" should be amended to --meq/g, and--.

Signed and Sealed this

Twenty-fifth Day of July, 1995

Attest:

BRUCE LEHMAN

*Attesting Officer*    *Commissioner of Patents and Trademarks*